(12) United States Patent
Becker et al.

(10) Patent No.: US 9,090,528 B2
(45) Date of Patent: Jul. 28, 2015

(54) HYDROALKYLATION PROCESS

(71) Applicant: ExxonMobil Chemical Patents Inc., Baytown, TX (US)

(72) Inventors: Christopher L. Becker, Manhattan, KS (US); James R. Lattner, LaPorte, TX (US); Keith H. Kuechler, Friendswood, TX (US); Hari Nair, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/375,967

(22) PCT Filed: Nov. 30, 2012

(86) PCT No.: PCT/US2012/067445
§ 371 (c)(1),
(2) Date: Jul. 31, 2014

(87) PCT Pub. No.: WO2013/130144
PCT Pub. Date: Sep. 6, 2013

(65) Prior Publication Data
US 2015/0005531 A1    Jan. 1, 2015

Related U.S. Application Data

(60) Provisional application No. 61/603,510, filed on Feb. 27, 2012.

(30) Foreign Application Priority Data

Mar. 30, 2012 (EP) ..................................... 12162355

(51) Int. Cl.
| | |
|---|---|
| C07C 45/53 | (2006.01) |
| C07C 37/08 | (2006.01) |
| C07C 2/74 | (2006.01) |
| C07C 5/32 | (2006.01) |
| C07C 5/367 | (2006.01) |

(52) U.S. Cl.
CPC . *C07C 2/74* (2013.01); *C07C 5/321* (2013.01); *C07C 5/367* (2013.01); *C07C 37/08* (2013.01); *C07C 45/53* (2013.01); *C07C 2101/14* (2013.01); *C07C 2521/00* (2013.01); *C07C 2523/00* (2013.01); *C07C 2529/74* (2013.01)

(58) Field of Classification Search
CPC .......... C07C 45/53; C07C 37/08; C07C 2/74; C07C 5/321

USPC ........................... 568/342, 798; 585/252, 467
See application file for complete search history.

(56) References Cited

U.S. PATENT DOCUMENTS

| | | | | |
|---|---|---|---|---|
| 3,354,078 | A | * | 11/1967 | Miale et al. ................. 208/120.1 |
| 4,439,409 | A | | 3/1984 | Puppe et al. |
| 4,826,667 | A | | 5/1989 | Zones et al. |
| 4,954,325 | A | | 9/1990 | Rubin et al. |
| 5,236,575 | A | | 8/1993 | Bennett et al. |
| 5,250,277 | A | | 10/1993 | Kresge et al. |
| 5,362,697 | A | | 11/1994 | Fung et al. |
| 6,037,513 | A | * | 3/2000 | Chang et al. ................... 585/467 |
| 6,049,018 | A | | 4/2000 | Calabro et al. |
| 6,077,498 | A | | 6/2000 | Cabañas et al. |
| 6,720,462 | B2 | | 4/2004 | Kuhnle et al. |
| 6,756,030 | B1 | | 6/2004 | Rohde et al. |
| 7,579,511 | B1 | * | 8/2009 | Dakka et al. ................... 585/316 |
| 2011/0037022 | A1 | * | 2/2011 | Dakka et al. ............. 252/182.31 |

FOREIGN PATENT DOCUMENTS

| | | |
|---|---|---|
| EP | 0 293 032 | 11/1988 |
| WO | WO 97/17290 | 5/1997 |
| WO | WO 2009/025939 | 2/2009 |
| WO | WO 2009/131769 | 10/2009 |

OTHER PUBLICATIONS

Weisz et al., "*Superactive Crystalline Aluminosilicate Hydrocarbon Catalyst*," Journal of Catalysis, vol. 4 (1965), pp. 527-529.
Miale et al., "*Catalysis by Crystalline Aluminosilicates IV. Attainable Catalytic Rate Constants, and Superactivity*," Journal of Catalysis, vol. 6 (1966), pp. 278-287.
Olson et al., "*Chemical and Physical Properties of the ZSM-5 Substitutional Series*," Journal of Catalysis, vol. 61, Issue 2 (Feb. 1980), pp. 390-396.

* cited by examiner

*Primary Examiner* — Sikarl Witherspoon
(74) *Attorney, Agent, or Firm* — Siwen Chen; Stephen A. Baehl

(57) ABSTRACT

In a process for producing phenol, benzene is hydroalkylated with hydrogen in the presence of a catalyst under conditions effective to produce a hydroalkylation reaction product comprising cyclohexylbenzene and cyclohexane. At least a portion of the cyclohexane from said hydroalkylation reaction product is then dehydrogenated to produce a dehydrogenation effluent comprising benzene, toluene and hydrogen. At least a portion of the dehydrogenation effluent is washed with a benzene-containing stream to transfer at least a portion of the toluene from the dehydrogenation effluent to the benzene-containing stream.

25 Claims, 1 Drawing Sheet

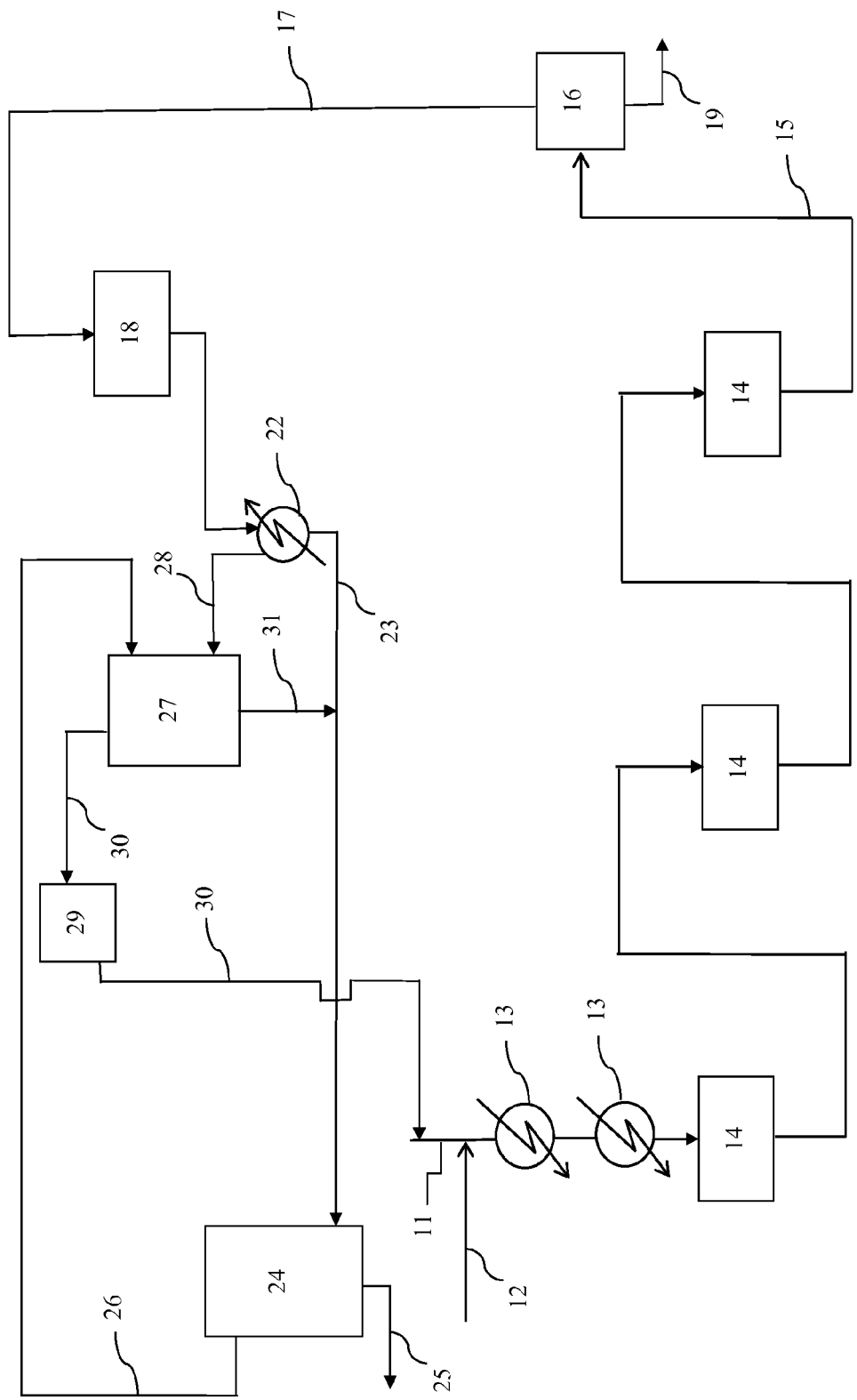

HYDROALKYLATION PROCESS

PRIORITY CLAIM TO RELATED APPLICATIONS

This application is a National Stage Application International Application No. PCT/US2012/067445 filed Nov. 30, 2012, which claims priority to U.S. Provisional Application Ser. No. 61/603,510 filed Feb. 27, 2012 and European Application No. 12162355.7 filed Mar. 30, 2012, the disclosures of which are fully incorporated herein by their reference.

FIELD

The present invention relates to a hydroalkylation process useful for making phenol.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process via cumene. This is a three-step process in which the first step involves alkylation of benzene with propylene in the presence of an acidic catalyst to produce cumene. The second step is oxidation, preferably aerobic oxidation, of the cumene to the corresponding cumene hydroperoxide. The third step is the cleavage of the cumene hydroperoxide generally in the presence of a sulfuric acid catalyst into equimolar amounts of phenol and acetone.

It is also known that phenol and cyclohexanone can be co-produced by a process in which cyclohexylbenzene is oxidized to obtain cyclohexylbenzene hydroperoxide and the hydroperoxide is decomposed in the presence of an acid catalyst to the desired phenol and cyclohexanone. Although various methods are available for the production of cyclohexylbenzene, a preferred route is disclosed in U.S. Pat. No. 6,037,513, in which the cyclohexylbenzene is produced by hydroalkylating benzene in the presence of a bifunctional catalyst comprising a molecular sieve of the MCM-22 family and at least one hydrogenation metal selected from palladium, ruthenium, nickel, cobalt and mixtures thereof. The '513 patent also discloses that the resultant cyclohexylbenzene can be oxidized to the corresponding hydroperoxide and then decomposed to the desired phenol and cyclohexanone co-product.

Although the process of the '513 patent is very selective in the conversion of benzene to cyclohexylbenzene, one inevitable by-product of the process is cyclohexane resulting from competing hydrogenation of the benzene feed and the cyclohexene intermediate. Not only does the cyclohexane by-product represent a significant loss of valuable benzene feed but its separation from the unreacted benzene by distillation is very difficult since the difference in boiling point between benzene and cyclohexane is only about 1° C. To obviate these problems, it has been proposed to selectively dehydrogenate the cyclohexane in the $C_6$ fraction of the hydroalkylation effluent to produce additional benzene and hydrogen. The unreacted benzene and the benzene and hydrogen produced by dehydrogenation of the cyclohexane can then be recycled to the hydroalkylation step. Examples of this process are disclosed in U.S. Pat. No. 7,579,511 and WO2009/131769.

Investigation of the cyclohexane dehydrogenation process has, however, now shown that the process produces small quantities, of the order of 1000 ppmw, of toluene which, if not removed, would be transported back to the hydroalkylation reactor in the benzene and hydrogen recycle streams. While the exact mechanism is unknown, it is believed the toluene may be produced through the decomposition of cyclohexylbenzene to form toluene and cyclopentane, or a methyl group from methylcyclopentane may react with benzene to form toluene. Toluene is a particularly disadvantageous impurity in the process since, following oxidation and cleavage, it leads to the production of cresols, which are difficult to remove from phenol and represent deleterious contaminants in the phenol product. Thus, the commercial application of dehydrogenation to remove cyclohexane from cyclohexylbenzene will also require removal of the co-produced toluene from the benzene and hydrogen product streams.

However, toluene is a known impurity in commercially available benzene streams, normally at a level of about 100 ppmw. Hence, in practice, any benzene feed used for production of cyclohexylbenzene by hydroalkylation will have to undergo prior treatment, normally by super-fractionation, to reduce the toluene level. Thus, in accordance with the present invention, the benzene recycle stream from the cyclohexane dehydrogenation step is fractionated to remove co-produced toluene and the resultant purified benzene is then used to wash, and thereby remove toluene entrained in the hydrogen recycle stream from the cyclohexane dehydrogenation step. The benzene wash liquid can then be fractionated to remove the toluene transferred from the hydrogen recycle stream. In general, a single super-fractionation column will be used to remove toluene from the feed benzene, the recycle benzene from the cyclohexane dehydrogenation step, and the benzene used to wash the hydrogen recycle from the cyclohexane dehydrogenation step.

SUMMARY

In one aspect, the invention resides in a hydroalkylation process comprising:
(a) hydroalkylating benzene with hydrogen in the presence of a catalyst under conditions effective to produce a hydroalkylation reaction product comprising cyclohexylbenzene, and cyclohexane;
(b) contacting at least a portion of the hydroalkylation reaction product with a dehydrogenation catalyst to produce a dehydrogenation effluent having at least a portion of the cyclohexane converted to benzene and hydrogen, wherein the dehydrogenation effluent further comprises toluene; and
(c) washing at least a portion of the dehydrogenation effluent with a benzene-containing stream to produce a toluene-depleted dehydrogenation effluent and a wash stream containing at least a portion of the toluene from the dehydrogenation effluent, wherein the at least a portion of the dehydrogenation effluent is in the vapor phase and the benzene-containing stream is in the liquid phase.

In another aspect, the invention resides in a hydroalkylation process comprising:
(a) hydroalkylating benzene with hydrogen in the presence of a catalyst under conditions effective to produce a hydroalkylation reaction product comprising cyclohexylbenzene and cyclohexane;
(b) contacting at least a portion of the hydroalkylation reaction product with a dehydrogenation catalyst to produce a dehydrogenation effluent having at least a portion of the cyclohexane converted to benzene and hydrogen, wherein the dehydrogenation effluent further comprises toluene;

(c) separating said dehydrogenation effluent into a liquid stream containing benzene and toluene from said dehydrogenation effluent and a gas stream containing hydrogen and toluene from said dehydrogenation effluent;

(d) fractionating said liquid stream to produce a toluene-depleted and benzene-enriched overhead stream; and (e) washing the gas stream with a portion of said overhead stream to produce a toluene-depleted hydrogen stream and a wash stream containing benzene and toluene.

Conveniently, the liquid stream contains at least 60 wt % of the benzene and at least 60 wt % of the toluene from said dehydrogenation effluent and the gas stream contains at least 80 wt % of the hydrogen from the dehydrogenation effluent, the wt %s based upon the weight of the dehydrogenation effluent.

Conveniently, the overhead stream contains less than 40 wt % of the toluene and greater than 60 wt % of the benzene from the liquid stream, the wt % based upon the weight of the liquid stream.

Conveniently, the wash stream contains at least 80 wt % of the toluene from the gas stream, the wt % based upon the weight of the gas stream.

In one embodiment, the gas stream flows countercurrent to said overhead stream in said washing (e). Typically, the washing (e) is conducted at a temperature between about 10° C. and about 160° C., more preferably between about 40° C. and about 140° C.

Conveniently, the ratio of benzene in the overhead stream to the benzene entrained in the gas stream is at least 1, or at least 1.2, or 1.2 to 1.4.

Conveniently, the toluene content of the gas stream is at least 5 ppmw, preferably at least 10 ppmw, and the toluene content of the toluene-depleted hydrogen stream is less than 5 ppmw, preferably less than 1 ppmw.

In one embodiment, the toluene-depleted hydrogen stream is recycled to (a), optionally after being compressed. Typically, the wash stream is recycled to (d).

In one embodiment, the process further comprises:
(i) providing a benzene feed containing toluene as an impurity to said fractionating (d); and
(ii) supplying part of the overhead stream to the hydroalkylating (a).

Generally, the dehydrogenation catalyst comprises (i) 0.05 wt % to 5 wt % of a metal selected from Group 14 of the Periodic Table of Elements, such as tin; and (ii) 0.1 wt % to 10 wt % of a metal selected from Groups 6 to 10 of the Periodic Table of Elements, such as platinum or palladium, the wt %s based upon total weight of the dehydrogenation catalyst.

Typically, the contacting (b) is conducted under dehydrogenation conditions comprising a temperature between 200° C. and 550° C. and a pressure between 100 kPa and 7,000 kPa.

In one embodiment, the process further comprises:
(f) recovering cyclohexylbenzene from said hydroalkylation reaction product;
(g) oxidizing at least a portion of the cyclohexylbenzene recovered in (f) to cyclohexylbenzene hydroperoxide; and
(h) cleaving at least a portion of the cyclohexylbenzene hydroperoxide produced in (g) to produce phenol and cyclohexanone.

BRIEF DESCRIPTION OF THE DRAWINGS

FIG. 1 is a schematic drawing of part of an integrated process for producing phenol from benzene according to one embodiment of the invention.

DETAILED DESCRIPTION OF THE EMBODIMENTS

Described herein is a process for producing phenol from benzene in which the benzene is hydroalkylated to produce cyclohexylbenzene and the cyclohexylbenzene is oxidized to produce cyclohexylbenzene hydroperoxide, which is subsequently cleaved to produce phenol and cyclohexanone. A by-product of the hydroalkylation reaction is cyclohexane which, because of the similarity of its boiling point with that of benzene, is removed from the hydroalkylation product by dehydrogenation to benzene together with a small amount of toluene impurity. Toluene is also ubiquitous impurity in commercial grade benzene and, so to avoid the production of cresols in the subsequent oxidation and cleavage steps, the present process provides a cost-effective scheme for reducing the level of toluene in the benzene and hydrogen recycle streams of the hydroalkylation process.

Production of the Cyclohexylbenzene

One step of an integrated process for producing phenol is the selective hydrogenation of benzene in the presence of a bifunctional hydroalkylation catalyst. The hydroalkylation reaction produces cyclohexylbenzene (CHB) according to the following reaction:

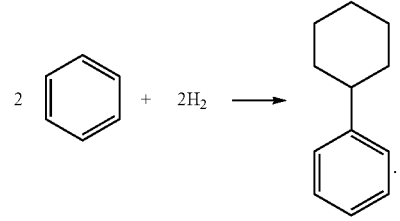 [SMILES: c1ccccc1 ; c1ccc(C2CCCCC2)cc1]

Any commercially available benzene feed can be used in the hydroalkylation reaction, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen. Generally, the benzene feed will contain at least 100 ppmw of toluene.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Typically, the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is present in the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56, and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from, but composited with, the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27, (1985).

The hydrogenation metal is deposited on the inorganic oxide, conveniently by impregnation, before the metal-containing inorganic oxide is composited with said molecular sieve. Typically, the catalyst composite is produced by co-pelletization, in which a mixture of the molecular sieve and the metal-containing inorganic oxide are formed into pellets at high pressure (generally about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays, which can be used as a binder, include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification. Suitable metal oxide binders include silica, alumina, zirconia, titania, silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia.

Treatment of the Cyclohexylbenzene Product

Although the hydroalkylation reaction using an MCM-22 family zeolite catalyst is highly selective towards cyclohexylbenzene, the hydroalkylation reaction will inevitably produce certain by-products. As stated previously, a prevalent by-product is normally cyclohexane but generally the reaction effluent will also contain dicyclohexylbenzene, tri-cyclobenzene and even heavier alkylates, and methylcyclopentane. Methylcyclopentane is also generated in the transalkylation reaction described in more detail below.

In the present process, the cyclohexane by-product is removed from the hydroalkylation reaction effluent by dehydrogenation to produce additional benzene that can be recycled to the hydroalkylation step.

In one embodiment, the dehydrogenation reaction is performed on all or an aliquot of the hydroalkylation reaction effluent.

In another embodiment, the hydroalkylation reaction effluent is fractionated before the dehydrogenation process into at least a (i) $C_6$-rich fraction, and (ii) a heavy fraction containing most of the cyclohexylbenzene and most of the dicyclohexylbenzene. The $C_6$-rich fraction contains unreacted benzene and methylcyclopentane in addition to cyclohexane, but the similar boiling points of these materials makes it difficult to separate them by distillation and hence the entire $C_6$-rich fraction is subjected to dehydrogenation.

It is to be appreciated that when a composition is described herein as being "rich in" or "enriched" in a specified species (e.g., $C_6$-rich, benzene-enriched or hydrogen-rich), it is meant that the wt % of the specified species in that composition is greater than the feed composition (i.e., the input). In contrast, when a composition is described as being "depleted in" a specified species (e.g., benzene-depleted), it is meant that the wt % of the specified species in that composition is depleted relative to the feed composition (i.e., the input). A "$C_6$" species generally means any species containing 6 carbon atoms.

The dehydrogenation process is conducted by contacting the hydroalkylation reaction effluent or the $C_6$-rich fraction thereof with a dehydrogenation catalyst under dehydrogenation conditions comprising a temperature between 200° C. and 550° C. and a pressure between 100 kPa and 7,000 kPa. Typically, the dehydrogenation catalyst comprises (i) 0.05 wt % to 5 wt % of a metal selected from Group 14 of the Periodic Table of Elements, such as tin; and (ii) 0.1 wt % to 10 wt % of a metal selected from Groups 6 to 10 of the Periodic Table of Elements, such as platinum or palladium, the wt %s based upon total weight of the dehydrogenation catalyst. In addition, the dehydrogenation catalyst further comprises a support which is typically selected from the group consisting of silica, alumina, a silicate, an aluminosilicate, zirconia, carbon, and carbon nanotubes.

The dehydrogenation catalyst is typically prepared by sequentially or simultaneously treating the support, such as by impregnation, with one or more liquid compositions comprising the Group 6-10 metal or a precursor thereof, the Group 14 metal or a precursor thereof and/or the optional inorganic base component or a precursor in a liquid carrier, such as water. An organic dispersant may be added to each liquid carrier to assist in uniform application of the metal component(s) to the support. Suitable organic dispersants include amino alcohols and amino acids, such as arginine. Generally, the organic dispersant is present in the liquid composition in an amount between 1 wt % and 20 wt % of the liquid composition.

In one preferred embodiment, the catalyst is prepared by sequential impregnation with the Group 14 metal component being applied to the support before the Group 6-10 metal component.

After treatment with the liquid composition, the support is heated in one or more stages, generally at a temperature of 100° C. to 700° C. for a time of 0.5 to 50 hours, to effect one or more of: (a) removal of the liquid carrier; (b) conversion of a metal component to a catalytically active form; and (c) decompose the organic dispersant. The heating may be conducted in an oxidizing atmosphere, such as air, or under reducing atmosphere conditions, such as hydrogen. After treatment with a liquid composition, the support is generally heated at a temperature of 200° C. to 500° C., such as 300° C. to 450° C., for a time of 1 to 10 hours.

In one embodiment, the dehydrogenation catalyst has an oxygen chemisorption value of greater than 5%, such as greater than 10%, for example greater than 15%, even greater than 20%, greater than 25%, or even greater than 30%. As used herein, the oxygen chemisorption value of a particular catalyst is a measure of metal dispersion on the catalyst and is defined as [the ratio of the number of moles of atomic oxygen sorbed by the catalyst to the number of moles of dehydrogenation metal contained by the catalyst]*100%. The oxygen chemisorption values referred to herein are measured using the following technique. Oxygen chemisorption measurements are obtained using the Micromeritics ASAP 2010. Approximately 0.3 to 0.5 grams of catalyst are placed in the Micrometrics device. Under flowing helium, the catalyst is ramped from ambient (i.e., 18° C.) to 250° C. at a rate of 10° C. per minute and held for 5 minutes. After 5 minutes, the sample is placed under vacuum at 250° C. for 30 minutes. After 30 minutes of vacuum, the sample is cooled to 35° C. at 20° C. per minute and held for 5 minutes. The oxygen and hydrogen isotherm is collected in increments at 35° C. between 0.50 and 760 mm Hg. Extrapolation of the linear portion of this curve to zero pressure gives the total (i.e., combined) adsorption uptake.

Preferably, the alpha value of the dehydrogenation catalyst is from 0 to 10, and from 0 to 5, and from 0 to 1. The alpha value of the support is an approximate indication of the catalytic cracking activity of the catalyst compared to a standard catalyst. The alpha test gives the relative rate constant (rate of normal hexane conversion per volume of catalyst per unit time) of the test catalyst relative to the standard catalyst which is taken as an alpha of 1 (Rate Constant=0.016 $sec^{-1}$). The alpha test is described in U.S. Pat. No. 3,354,078 and in J. Catalysis, 4, 527, (1965); 6, 278, (1966); and 61, 395, (1980), to which reference is made for a description of the test. The experimental conditions of the test used to determine the alpha values referred to in this specification include a constant temperature of 538° C. and a variable flow rate as described in detail in J. Catalysis, 61, 395, (1980).

In addition to converting the cyclohexane to additional benzene, the dehydrogenation process inherently also produces toluene which, as stated above, will also usually be present in the benzene feed. However, toluene is a particularly disadvantageous impurity in the process since, following oxidation and cleavage, it leads to the production of cresols which are difficult to remove from phenol and represent deleterious contaminants in the phenol product. Thus the present process seeks to reduce the toluene level in the benzene and hydrogen recycle streams to the hydroalkylation process to very low levels, such as less than 5 ppmw, preferably less than 1 ppmw.

In particular, the effluent from the dehydrogenation process may be initially separated into a liquid stream containing most, that is at least 50 wt %, normally at least 60 wt %, normally at least 80 wt % of the benzene and toluene in the dehydrogenation effluent and a gas stream containing most, that is at least 50 wt %, normally at least 80 wt %, of the hydrogen in the dehydrogenation effluent, together with at least some toluene in the dehydrogenation effluent. The liquid stream is then fractionated, normally by super-fractionation, to produce a toluene-depleted and benzene-enriched overhead stream which typically contains less than 40 wt %, such as less than 20 wt %, of the toluene from the liquid stream and greater than 60 wt %, such as greater than 80 wt %, such as greater than 90 wt %, such as greater than 99.8 wt % of the benzene from the liquid stream.

The overhead stream is then used to wash the gas stream, normally in a countercurrent wash column and conveniently at a temperature between about 10° C. and about 160° C., such as between about 40° C. and about 140° C. Typically, the ratio of benzene in the overhead stream to the benzene entrained in the gas stream is at least 1, generally at least 1.2, and preferably about 1.2 to about 1.4. The washing removes most of the toluene from the gas stream so as to produce a toluene-depleted hydrogen stream and a wash stream containing benzene and toluene. In this way, with the gas stream having a toluene content of at least 5 ppmw, or even at least 10 ppmw, the toluene content of the toluene-depleted hydrogen stream can be reduced to less than 5 ppmw, even less than 1 ppmw.

The toluene-depleted hydrogen stream can then be recycled to the hydroalkylation step, whereas the wash stream is generally recycled to the super-fractionation step.

As discussed above, fractionation of the hydroalkylation reaction effluent produces a heavy fraction in addition to the $C_6$-rich fraction. This heavy fraction is further fractionated to produce a $C_{12}$-rich fraction containing most of the cyclohexylbenzene and a $C_{18}$-rich fraction containing most of the dicyclohexylbenzene. The cyclohexylbenzene is fed to the oxidation step discussed below whereas, depending on the amount of the dicyclohexylbenzene produced, it may be desirable to either (a) transalkylate the dicyclohexylbenzene with additional benzene, or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 $hr^{-1}$ to about 10 $hr^{-1}$ on total feed, and a benzene/dicyclohexylbenzene weight ratio about of 1:1 to about 5:1. The transalkylation reaction can, and typically will, generate additional methylcyclopentane.

Dealkylation or cracking is also typically effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia, and mixtures thereof. Generally, the acid catalyst includes at least one aluminosilicate, aluminophosphate, or silicoaluminphosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically is from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

It is to be appreciated that the transalkylation and dealkylation reactions can, and typically will generate, additional methylcyclopentane and hence the products of these reactions can be subjected to the separation steps described above to generate the $C_6$ fraction(s), which may subsequently be subjected to dehydrogenation.

Cyclohexylbenzene Oxidation

In order to convert the cyclohexylbenzene into phenol and cyclohexanone, the cyclohexylbenzene may be oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air, or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N', N"-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent may be subjected to a cleavage reaction, with or without undergoing any prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3A molecular sieve, to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Publication No. WO 2009/025939.

Hydroperoxide Cleavage

Another reactive step in the conversion of the cyclohexylbenzene into phenol and cyclohexanone involves the acid-catalyzed cleavage of the cyclohexyl-1-phenyl-1-hydroperoxide produced in the oxidation step.

Generally, the acid catalyst used in the cleavage reaction is at least partially soluble in the cleavage reaction mixture, is stable at a temperature of at least 185° C. and has a lower volatility (higher normal boiling point) than cyclohexylbenzene. Typically, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm to and to no greater than 3000 wppm, or at least 150 wppm to and no greater than 2000 wppm of the acid catalyst, or at least 300 wppm and no greater than 1500 wppm of the acid catalyst, based upon total weight of the cleavage reaction mixture.

In other embodiments, a heterogeneous acid catalyst is employed for the cleavage reaction, such as molecular sieve, and in particular a molecular sieve having a pore size in excess of 7 Å. Examples of suitable molecular sieves include zeolite beta, zeolite Y, zeolite X, ZSM-12, and mordenite. In one embodiment, the molecular sieve comprises a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from about 20 wt % to about 80 wt % of the zeolite.

The cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction, but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

Generally, the cleavage reaction is conducted under conditions including a temperature of about 20° C. to about 200° C., such as about 40° C. to about 120° C. and a pressure of about 100 kPa to about 2000 kPa, such as about 100 kPa to about 1000 kPa, such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam and nylons, such as nylon 6 and nylon 6,6.

The phenol produced through the processes disclosed herein may be used, for example, to produce phenolic resins, bisphenol A, ε-caprolactam, adipic acid and/or plasticizers.

The invention will now be more particularly described with reference to the accompanying drawings and the following non-limiting Examples.

Referring to the drawings, FIG. 1 illustrates part of an integrated process for producing phenol according to a first embodiment of the invention. In this process hydrogen from line 11 is mixed with benzene from line 12 and the resultant mixed stream is heated by heat exchangers 13 before being fed to the first of three vertically disposed, series-connected hydroalkylation reactors 14. Each of the reactors 14 contains hydroalkylation catalyst and is operated under conditions such that benzene and hydrogen in the feed react to produce cyclohexylbenzene together with the by-products discussed above.

The hydroalkylation reaction product exiting the final reactor 14 is composed mostly of cyclohexylbenzene, dicyclohexylbenzene, cyclohexane and unreacted benzene. This product is fed by line 15 to a first distillation column 16 where a $C_6$-rich overhead stream containing most of the cyclohexane and unreacted benzene is removed and fed by line 17 to a dehydrogenation reactor 18. The bottoms from the first distillation column 16 contain most of the cyclohexylbenzene and dicyclohexylbenzene in the product effluent and is removed via line 19 for recovery of the cyclohexylbenzene.

The dehydrogenation reactor 18 converts at least a portion of the cyclohexane in the $C_6$-rich overhead stream to benzene and some toluene and the effluent from the dehydrogenation reactor 18 is fed to a cooler 22 where the effluent separates into a liquid stream containing most of the benzene and toluene and a gas stream containing most of the hydrogen and at least some of the toluene from the effluent.

The liquid stream is fed by line 23 to the main benzene fractionator 24 where the heavies including toluene are removed as a bottoms stream via line 25 to leave a toluene-depleted and benzene-enriched overhead stream, which is fed by line 26 to a wash column 27. The liquid overhead stream enters the top of the column 27 and flows countercurrent to the gas stream which is fed into the bottom of the column 27 by line 28. The liquid overhead stream removes toluene from the gas stream so that a toluene-depleted hydrogen stream flows out of the top of the column 27 via line 30 while a wash stream containing benzene and toluene exits the bottom of the column 27 via line 31. The hydrogen stream 30 is compressed in compressor 29 before being fed to line 11, while the wash stream is combined with liquid stream in line 23 and fed to the fractionator 24.

The invention claimed is:

1. A hydroalkylation process comprising:
   (a) hydroalkylating benzene with hydrogen in the presence of a catalyst under conditions effective to produce a hydroalkylation reaction product comprising cyclohexylbenzene and cyclohexane;
   (b) contacting at least a portion of the hydroalkylation reaction product with a dehydrogenation catalyst to produce a dehydrogenation effluent having at least a portion of the cyclohexane converted to benzene and hydrogen, wherein the dehydrogenation effluent further comprises toluene; and
   (c) washing at least a portion of the dehydrogenation effluent with a benzene-containing stream to produce a toluene-depleted dehydrogenation effluent and a wash stream containing at least a portion of the toluene from the dehydrogenation effluent, wherein the at least a portion of the dehydrogenation effluent is in the vapor phase and the benzene-containing stream is in the liquid phase.

2. The process of claim 1, wherein the at least a portion of the dehydrogenation effluent contains at least 50 wt % hydrogen, the wt % based upon the weight of the at least a portion of the dehydrogenation effluent.

3. The process of claim 1, wherein at least a portion of the toluene in the dehydrogenation effluent is formed from the decomposition of the cyclohexylbenzene.

4. The process of claim 1, wherein the wash stream contains at least 80 wt % of the toluene from the dehydrogenation effluent, the wt % based upon the weight of the dehydrogenation effluent.

5. A hydroalkylation process comprising:
   (a) hydroalkylating benzene with hydrogen in the presence of a catalyst under conditions effective to produce a hydroalkylation reaction product comprising cyclohexylbenzene and cyclohexane;
   (b) contacting at least a portion of the hydroalkylation reaction product with a dehydrogenation catalyst to produce a dehydrogenation effluent having at least a portion of the cyclohexane converted to benzene and hydrogen, wherein the dehydrogenation effluent further comprises toluene;
   (c) separating said dehydrogenation effluent into a liquid stream containing benzene and toluene from said dehydrogenation effluent and a gas stream containing hydrogen and toluene from said dehydrogenation effluent;
   (d) fractionating said liquid stream to produce a toluene-depleted and benzene-enriched overhead stream; and
   (e) washing the gas stream with a portion of said overhead stream to produce a toluene-depleted hydrogen stream and a wash stream containing benzene and toluene.

6. The process of claim 5, wherein the liquid stream contains at least 60 wt % of the benzene and at least 60 wt % of the toluene from said dehydrogenation effluent, the wt % based upon the weight of the dehydrogenation effluent.

7. The process of claim 5, wherein the gas stream contains at least 80 wt % of the hydrogen from the dehydrogenation effluent, the wt % based upon the weight of the dehydrogenation effluent.

8. The process of claim 5, wherein the overhead stream contains less than 40 wt % of the toluene from the liquid stream, the wt % based upon the weight of the liquid stream.

9. The process of claim 5, wherein the overhead stream contains greater than 60 wt % of the benzene from the liquid stream, the wt % based upon the weight of the liquid stream.

10. The process of claim 5, wherein the wash stream contains at least 80 wt % of the toluene from the gas stream, the wt % based upon the weight of the gas stream.

11. The process of claim 5, wherein the gas stream flows countercurrent to said overhead stream in the washing (e).

12. The process of claim 5, wherein the washing (e) is conducted at a temperature between about 10° C. and about 160° C.

13. The process of claim 5, wherein the washing (e) is conducted at a temperature between about 40° C. and about 140° C.

14. The process of claim 5, wherein the ratio of benzene in the overhead stream to the benzene entrained in the gas stream is at least 1.

15. The process of claim 5, wherein the ratio of benzene in the overhead stream to the benzene entrained in the gas stream is about 1.2 to about 1.4.

16. The process of claim 5, wherein the toluene content of the gas stream is at least 5 ppmw and the toluene content of the toluene-depleted hydrogen stream is less than 5 ppmw.

17. The process of claim 5, wherein the toluene content of the gas stream is at least 10 ppmw and the toluene content of the toluene-depleted hydrogen stream is less than 1 ppmw.

18. The process of claim 5, wherein at least a portion of the toluene-depleted hydrogen stream is recycled to (a).

19. The process of claim 5, wherein at least a portion of the toluene-depleted hydrogen stream is compressed before being recycled to the hydroalkylating (a).

20. The process of claim 5, wherein at least a portion of the wash stream is recycled to (d) to remove at least a portion of the toluene and recycled to hydroalkylating (a).

21. The process of claim 5, and further comprising:
   (i) providing a benzene feed containing toluene as an impurity to said fractionating (d); and
   (ii) supplying a portion of the overhead stream to (a).

22. The process of claim 5, wherein the dehydrogenation catalyst comprises: (i) 0.05 wt % to 5 wt % of a metal selected from Group 14 of the Periodic Table of Elements; and (ii) 0.1 wt % to 10 wt % of a metal selected from Groups 6 to 10 of the Periodic Table of Elements, the wt %s based upon total weight of the dehydrogenation catalyst.

23. The process of claim 22, wherein the metal selected from Group 14 of the Periodic Table of Elements is tin and the metal selected from Groups 6 to 10 of the Periodic Table of Elements is platinum or palladium.

24. The process of claim 5, wherein the contacting (b) is conducted under dehydrogenation conditions comprising a temperature between 200° C. and 550° C. and a pressure between 100 kPa and 7,000 kPa.

25. The process of claim 5, and further comprising:
   (f) recovering at least a portion of the cyclohexylbenzene from said hydroalkylation reaction product;
   (g) oxidizing at least a portion of the cyclohexylbenzene recovered in (f) to cyclohexylbenzene hydroperoxide; and
   (h) cleaving at least a portion of the cyclohexylbenzene hydroperoxide produced in (g) to produce phenol and cyclohexanone.

\* \* \* \* \*